United States Patent [19]
Seyl

[11] Patent Number: 5,980,472
[45] Date of Patent: Nov. 9, 1999

[54] JOINT MOVEMENT MONITORING SYSTEM

[76] Inventor: V. Craig Seyl, 9860 Pflumm Rd., Lenexa, Kans. 66215

[21] Appl. No.: 09/026,834

[22] Filed: Feb. 20, 1998

[51] Int. Cl.⁶ .................................................. A61B 5/103
[52] U.S. Cl. ........................................... 600/587; 600/595
[58] Field of Search ................................... 600/587, 779, 600/595

[56] References Cited

U.S. PATENT DOCUMENTS

| | | |
|---|---|---|
| 3,258,007 | 6/1966 | Karpovich et al. . |
| 4,436,099 | 3/1984 | Raftopoulos . |
| 4,444,205 | 4/1984 | Jackson . |
| 4,542,291 | 9/1985 | Zimmerman . |
| 4,665,928 | 5/1987 | Linial et al. . |
| 4,774,966 | 10/1988 | Lemmen . |
| 4,922,925 | 5/1990 | Crandall et al. . |
| 5,215,100 | 6/1993 | Spitz et al. . |
| 5,230,345 | 7/1993 | Curran et al. . |

FOREIGN PATENT DOCUMENTS

WO 94/01042  1/1994  WIPO ............................. A61B 5/103

*Primary Examiner*—Cary O'Connor
*Assistant Examiner*—Pamela Wingood
*Attorney, Agent, or Firm*—Hovey, Williams, Timmons & Collins

[57] ABSTRACT

A preferred joint movement monitoring system (10) includes a carrier (18) configured for wearing by a subject about a wrist thereof and a plurality of position sensors (12, 14, 16) coupled with the carrier (18) for sensing various hand positions of the subject. The preferred carrier (18) is in the form of an elastic wrist band that encompasses the wrist and adjacent portions of the hand and forearm without covering any portions of the subject's fingers. The preferred sensors (12, 14, 16) include Hall effect sensors mounted to the carrier (18) on the forearm side of the wrist.

11 Claims, 3 Drawing Sheets

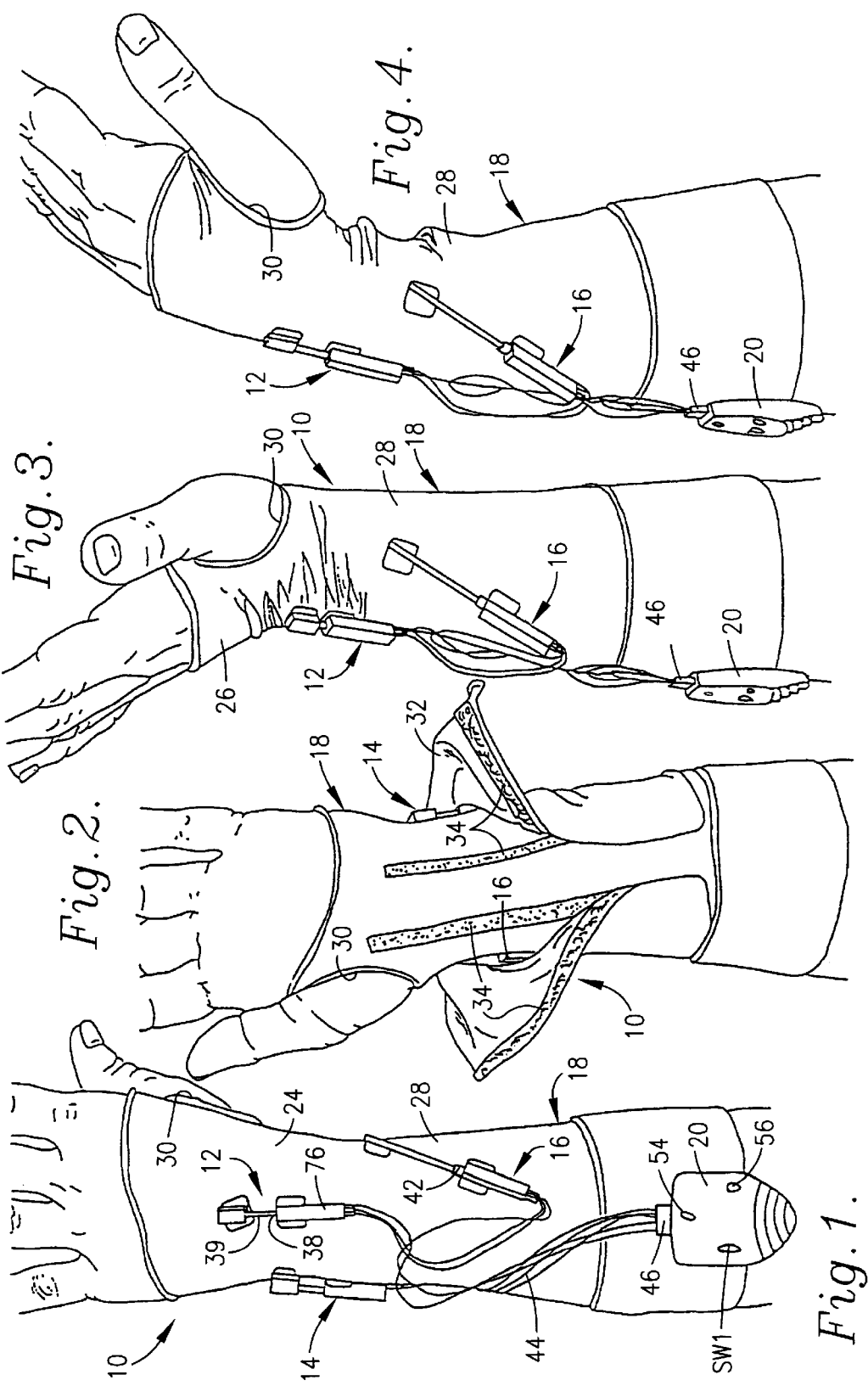

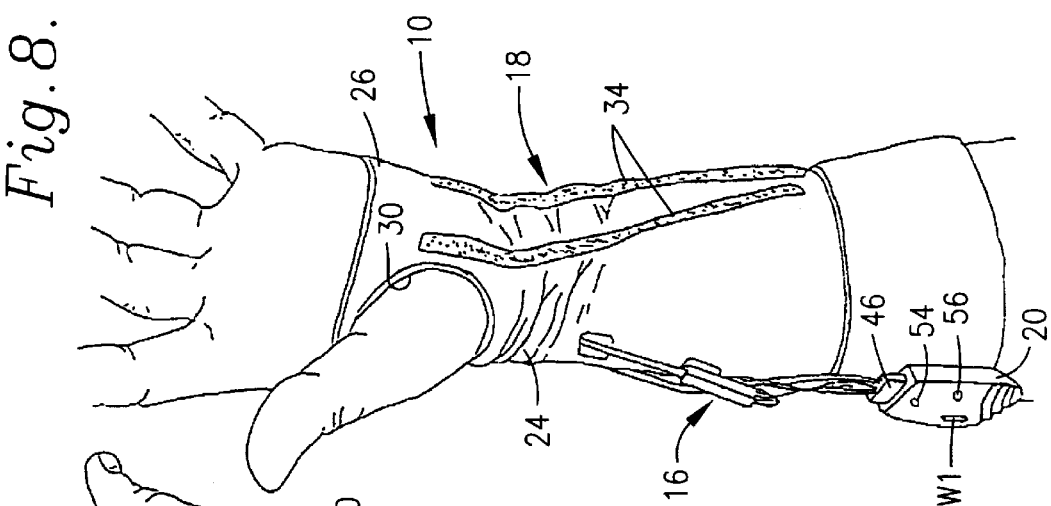
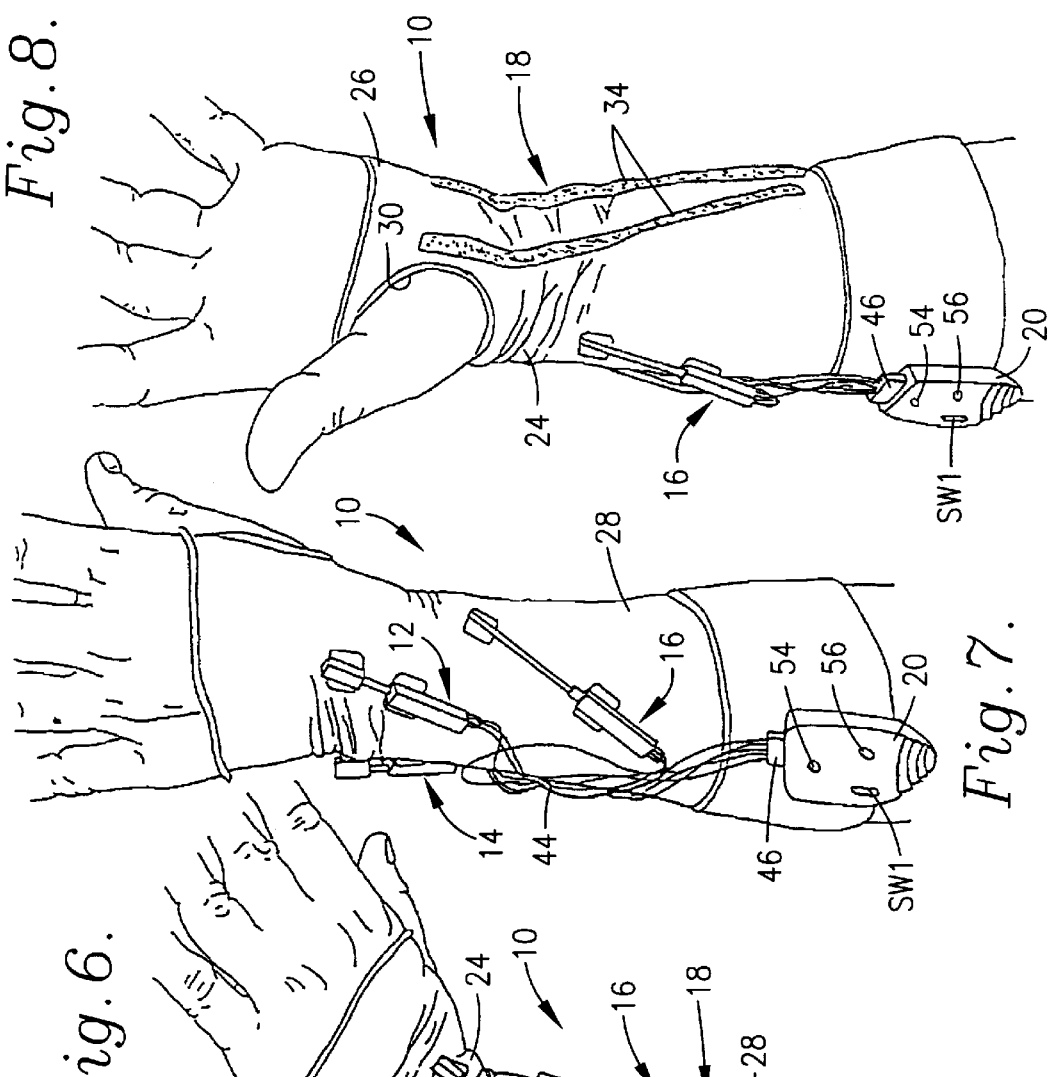
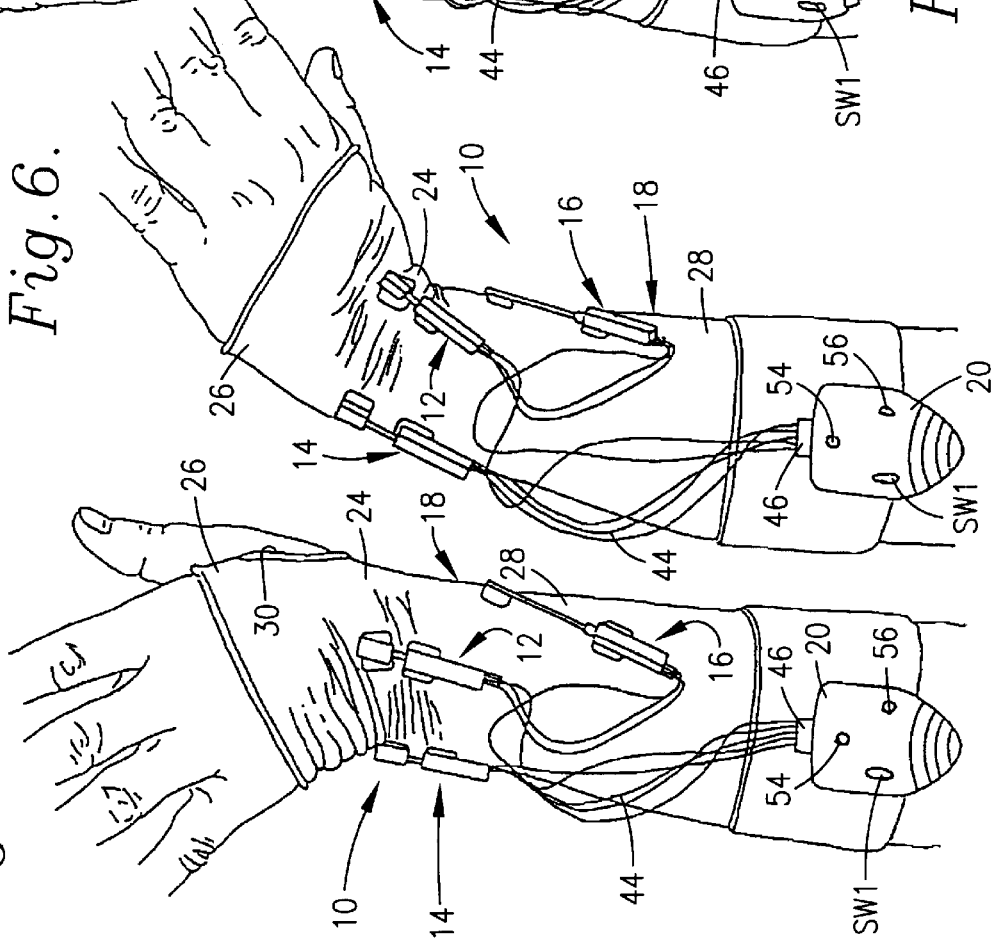

1

JOINT MOVEMENT MONITORING SYSTEM

MICROFICHE APPENDIX

A microfiche appendix as Appendix 1 containing a source code of a computer program useful in accordance with the present invention is appended hereto as 3 sheet(s) of microfiche containing 186 frames.

RELATED APPLICATIONS

Not applicable.

FEDERALLY SPONSORED RESEARCH OR DEVELOPMENT

Not applicable.

BACKGROUND OF THE INVENTION

1. Field of the Invention

The present invention is concerned with the field of monitoring joint movements of a subject. In particular, a preferred joint movement monitoring system includes a carrier configured for wearing by a subject about a wrist thereof and a plurality of position sensors coupled with the carrier for sensing various hand positions of the subject.

2. Description of the Prior Art

With advances in medical science, it is now better appreciated that repetitive motion can sometimes lead to injury such as carpal tunnel syndrome. In response, devices have been developed to monitor the motions of body parts with respect to a joint.

One such device includes a glove with portions of the glove fingers removed and with sensors positioned adjacent the back of the hand. Such a device inhibits natural motion of the fingers and of the hand itself, leading to less realistic data. Moreover, the bulk of the glove is sometimes objectionable by wearers.

SUMMARY OF THE INVENTION

The present invention solves the prior art problems mentioned above and provides a distinct advance in the state of the art. In particular, the joint movement monitoring system hereof enables the gathering of accurate data using a comfortable appliance and without inhibiting the wearer's natural movements.

The preferred embodiment of the present invention includes a plurality of position sensors, a carrier mounting the sensors and configured for wearing by the subject and for positioning the sensors adjacent the wrist of the subject, and a controller for storing position data received from the sensors and representative of hand positions. In preferred forms, the active components of the sensors are Hall effect sensors mounted on the carrier adjacent the subject's forearm rather than the subject's hand. The preferred carrier is an elastic band encompassing the wrist and adjacent portions of the hand and forearm without covering any portion of the fingers of the subject's hand.

BRIEF DESCRIPTION OF THE DRAWINGS

FIG. 1 is a front view of the preferred apparatus in accordance with the present invention showing the cover removed for clarity of illustration and shown being worn by a subject;

FIG. 2 is a rear view of the apparatus of FIG. 1 with the cover partially removed for clarity of illustration;

FIG. 3 is a right side view of the apparatus of FIG. 1 with the subject's hand in flexion;

FIG. 4 is a view similar to FIG. 3 with the subject's hand in extension;

FIG. 5 is a front view of the apparatus of FIG. 1 with the subject's hand in radial extension;

FIG. 6 is a front view of the apparatus of FIG. 1 with the subject's hand in ulnar extension;

FIG. 7 is a front view of the apparatus of FIG. 1 with the subject's hand in pronation;

FIG. 8 is a view of the apparatus of FIG. 1 with the subject's hand in supination.

DETAILED DESCRIPTION OF THE PREFERRED EMBODIMENT

Figure 9:
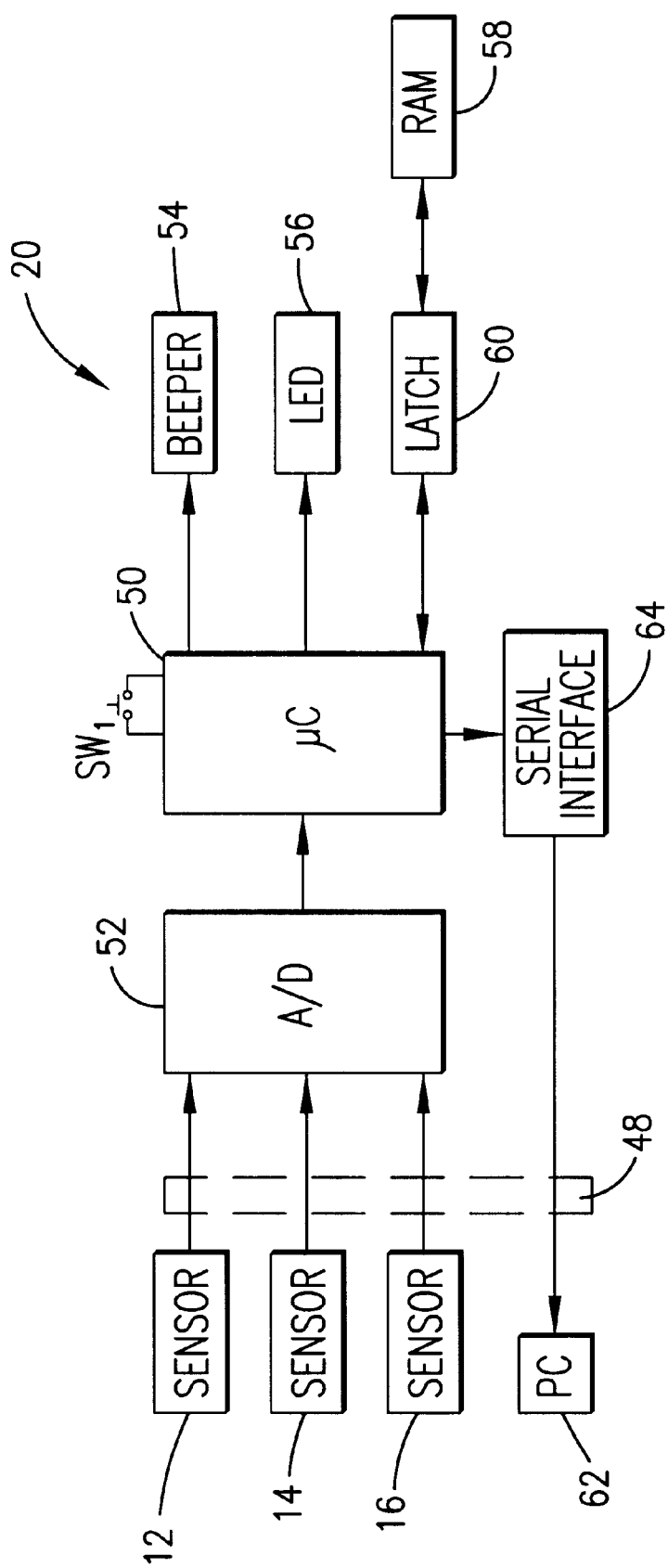
FIG. 9 is an electrical block diagram of the sensors and controller of FIG. 1 further connected with a personal computer.

The drawing figures illustrate preferred joint movement monitoring apparatus 10 in accordance with the present invention. Apparatus 10 broadly includes flexion/extension (up/down) sensor 12, ulnar/radial deviation (left/right) sensor 14, pronation/supination (rotation) sensor 16, carrier 18, controller 20 and in preferred forms, personal computer 22 (see FIG. 9).

Carrier 18 is preferably in the form of light weight, elastic band for wearing by a subject and includes wrist section 24 along with adjacent hand section 26 and forearm section 28 for substantially encompassing the respective body parts. Hand section 26 includes thumb hole 30 for positioning and orienting carrier 18 on a subject. As illustrated, carrier 18 is configured to position sensors 12–16 without covering any portion of the subject's fingers. Because of this, carrier 18 does not inhibit free movement of the subject's fingers, which has been a problem with prior art devices.

Carrier 18 also includes wrap-around cover 32 (See FIG. 2) for covering and protecting sensors 12–16. Cover 32 is secured using conventional hook-and-eye fasteners 34.

Each sensor 12–16 includes an active component and a static component. Each active component includes slide block 36 with a Hall effect sensor contained therein and positioned adjacent rod-receiving, slide opening 38 defined in block 36. As shown in FIGS. 1–5, each slide block 36 is mounted on forearm section 28 of carrier 18.

The static component is in the form of a sensor rod 39 having one end 40 affixed to carrier 18 and the distal end slidably received in the rod-receiving opening 38 of a corresponding slide block 36. The distal end of each sensor rod includes cylindrically shaped magnet 42 axially coupled therewith and positioned to slide within slide opening 38.

For sensors 12 and 14, it will be noted that end 40 of each sensor rod 39 is connected to hand section 26 of carrier 18 and that sensor rod 39 spans wrist section 24 and terminates within a respective slide block 36 mounted to forearm section 28. Sensor 16 is positioned entirely on forearm section 28. With this arrangement, the bulk of sensors 12 and 14 is off of the wearer's hand and does not inhibit the freedom of movement thereof which has been a problem in the prior art. Wires 44 couple each sensor 12–16 (and in particular, each Hall effect sensor thereof) with controller 20 by way of plug 46.

Each sensor 12–16 is operable for sensing hand positions of the subject as indicated by magnet 42 and for producing position signals representative thereof as discussed further herein. In particular, FIGS. 3 and 4 illustrate the operation of sensor 12 for sensing the extremes of flexion (FIG. 3), extension (FIG. 4) and positions therebetween. Similarly, FIGS. 5 and 6 illustrate the operation of sensor 14 for sensing the extremes of radial extension (FIG. 5), ulnar extension (FIG. 6) and positions therebetween.

As best viewed in FIG. 7, sensor 16 is mounted on forearm section 28 at an angle relative to the axis of carrier 18. This enables sensor 16 to sense the rotational positions of the wearer's hand by sensing rotation of the forearm. FIG. 7 illustrates the subject's forearm in pronation, that is, rotated in one direction and the position of sensor 16. FIG. 8 illustrates the subject's forearm rotated in the opposite direction (supination) and the position of sensor 16. As will now be appreciated, sensors 12–16 monitor all six degrees of hand movements illustrated in FIGS. 3–8 and thereby enable monitoring of all possible positions of the subject's hand.

Apparatus 10 is useful for monitoring the positions of a wearer's hand over time which represents movement and storing position data represented thereof. This data can then be analyzed to determine whether the subject is exposed to repetitive motion injury.

In use, the subject dons carrier 18 with sensors 12–16 and controller 20 attached thereto. The wearer's hand is inserted through thumb hole 30 and carrier 18 pulled snugly toward the wearer's elbow with sensor 12 centrally positioned (see FIG. 7) and with sensor 14 adjacent and aligned with the ulnar. Also, plug 46 is received in connector 48 (FIG. 9) of controller 20.

Referring to FIG. 9, normally open, switch SW1 is then depressed which activates microcontroller 50 (type 87051). Microcontroller 50 along with the other components of controller 20 and sensors 12–16 are powered by a conventional power supply including a battery (not shown) contained within the housing of controller 20.

A computer program (shown in the microfiche appendix included as part of the disclosure hereof) is stored within the internal ROM of microcontroller 50 and controls the operation thereof and thereby the operation of controller 20. Analog-to-digital converter (A/D) 52 receives the analog position signals from sensors 12–16 and converts these to digital position signals for use by microcontroller 50. Plug 46 is configured to connect with pins 1–6 of connector 48. Pins 8–10 are used for serial data transfer as further discussed below.

Upon activation by switch SW1, beeper 52 sounds a tone, LED 56 is activated indicating that controller 20 is operating, and microcontroller 50 begins sampling the position signals from sensors 12–16 at the programmable rate. Microcontroller 50 derives position data representative of the subject's hand positions from the position signals and stores this data in RAM (random access memory) 58 by way of latch 60. RAM 58 can store up to eight hours of position data for later analysis.

Upon completion of data gathering, the position data can then be transferred to personal computer 60 by way of RS232 serial interface 62. Specifically, plug 46 from sensors 12–16 is removed from connector 48 and replaced by a conventional serial plug (not shown) from PC 60 using pins 8–10 of connector 48. In the preferred embodiment, controller 20 is attached to carrier 18 using hook-and-eye fasteners. This allows controller 20 to be removed easily for connection to PC 60.

PC 60 is preferably a conventional personal computer such as a PENTIUM-based microcomputer using WINDOWS 95 operating system. The microfiche appendix, included as part of the disclosure hereof, illustrates the preferred program written in Visual Basic for analyzing the position data gathered by controller 20. The data can be displayed as a chart (deviation over time), a histogram (amount of time per quartile deviation), and a report in terms of a statistical analysis of the mean, average, and standard deviation. These analyses can be saved to disk or printed as is conventional.

The program is also operable to animate a hand moving in three dimensions on the screen. The hand can be viewed in real time, slow motion or frame by frame. The preferred animation technique uses screen display data representing about 2300 hand positions stored in mass storage. For position data indicating a given position of the subject's hand, the corresponding screen display data is retrieved to present a frame. This simple technique enables efficient presentation of the animation.

The present invention can also be used in a preventive mode. In this mode, user loads predetermined limits of position movement into RAM 58. The program operates microcontroller 50 to monitor the positions of the subject's hand as indicated by sensors 12–16. If the position of the hand reaches one of the indicated limits, beeper 54 is activated thereby providing an audible indication to the subject that a predetermined limit has been reached. By proper setting of these limits, the subject can be trained to avoid those extremes of positions that might lead to injury.

Those skilled in the art will appreciate that the present invention encompasses many variations in the preferred embodiment described herein. For example, the invention finds utility in monitoring the movement of other parts of the subject's body such as head and neck, the torso and back, and legs. Also, the utility is not limited to a human subject but could also include mechanical devices such as robots and the like. In addition, the invention encompasses sensors other than the preferred Hall effect that can monitor position or movement. Moreover, the controller can use other types of devices such as digital signal processors and the like.

Having thus described the preferred embodiment of the present invention, the following is claimed as new and desired to be secured by Letters Patent:

I claim:

1. A hand movement monitoring apparatus for monitoring the movement of a hand adjacent a wrist of a subject, said apparatus comprising:

a plurality of position sensors;

a carrier, carrying said sensors, configured for wearing by the subject and for positioning said sensors adjacent the wrist of a subject, said sensors including means for sensing a plurality of hand positions of the subject and for producing position signals representative thereof; and a controller including means for receiving and responding to said position signals for deriving position data therefrom representative of said hand positions and storing said position data, each of said sensors including an active component coupled with said carrier adjacent the forearm of the subject on the opposed side of the wrist as the hand, and a static component spanning the wrist and coupled with said carrier adjacent the hand of a subject.

2. The apparatus as set forth in claim 1, said static component including a sensor rod having one end coupled with said carrier adjacent the hand of the subject and with the other end thereof presenting a magnet, said active component including a slide block having a Hall effect sensor and a rod opening defined therein for slidably receiving said magnet.

3. The apparatus as set forth in claim 1, said carrier being configured for substantially encompassing the wrist and adjacent portions of the hand and forearm of the subject.

4. A hand movement monitoring apparatus for monitoring the movement of a hand adjacent a wrist of a subject, said apparatus comprising:

a plurality of position sensors;

a carrier, carrying said sensors, configured for wearing by the subject and for positioning said sensors adjacent the wrist of a subject, said sensors including means for sensing a plurality of hand positions of the subject and for producing position signals representative thereof; and a controller including means for receiving and responding to said position signals for deriving position data therefrom representative of said hand positions and storing said position data, said carrier being composed of elastic material and presenting a tubular configuration with a thumb hole defined adjacent one end thereof.

5. The apparatus as set forth in claim 1, said controller including means for transferring said position data to a computer.

6. The apparatus as set forth in claim 1, further including a personal computer having means for coupling with said controller and for receiving said position data therefrom, and means for analyzing said position data.

7. A hand movement monitoring apparatus for monitoring the movement of a hand adjacent a wrist of a subject, said apparatus comprising:

a plurality of position sensors;

a carrier, carrying said sensors, configured for wearing by the subject and for positioning said sensors adjacent the wrist of a subject, said sensors including means for sensing a plurality of hand positions of the subject and for producing position signals representative thereof; and a controller including means for receiving and responding to said position signals for deriving position data therefrom representative of said hand positions and storing said position data, said controller including means for determining whether said hand positions exceed a predetermined limit.

8. A hand movement monitoring apparatus for monitoring the movement of a hand adjacent a wrist of a subject, said apparatus comprising:

a plurality of position sensors;

a carrier, carrying said sensors, configured for wearing by the subject and for positioning said sensors adjacent the wrist of a subject, said sensors including means for sensing a plurality of hand positions of the subject and for producing position signals representative thereof; and a controller including means for receiving and responding to said position signals for deriving position data therefrom representative of said hand positions and storing said position data, said controller including means for producing an audible output if said hand positions exceed a predetermined limit.

9. A hand movement monitoring apparatus for monitoring the movement of a hand adjacent a wrist of a subject, said apparatus comprising:

a plurality of position sensors including a flexion/extension sensor, an ulnar/radial deviation sensor, and a pronation/supination sensor;

a carrier, carrying said sensors, configured for wearing by the subject and for positioning said sensors adjacent the wrist of a subject, said sensors including means for sensing a plurality of hand positions of the subject and for producing position signals representative thereof, each of said sensors including a sensor rod having one end coupled with said carrier and the distal end thereof presenting a magnet and a slide block with a rod opening defined therein for slidably receiving said magnet and a Hall effect sensor positioned for sensing said magnet; and a controller including means for receiving and responding to said position signals for deriving position data therefrom representative of said hand positions and storing said position data, said carrier being configured for positioning said sensors without covering any portion of the fingers of the hand.

10. The apparatus as set forth in claim 9, said controller including means for determining whether said hand positions exceed a predetermined limit.

11. The apparatus as set forth in claim 10, said controller including means for producing an audible output if said hand positions exceed a predetermined limit.

* * * * *